United States Patent
Rohner et al.

(10) Patent No.: US 9,931,188 B2
(45) Date of Patent: Apr. 3, 2018

(54) DENTAL COLOR KEY

(71) Applicant: Ivoclar Vivadent AG, Schaan (LI)

(72) Inventors: Gottfried Rohner, Alstatten (CH); Diethard Bertsch, Gofis (AT); Michael Brotzge, Koblach (AT)

(73) Assignee: Ivoclar Vivadent AG, Schaan (LI)

( * ) Notice: Subject to any disclaimer, the term of this patent is extended or adjusted under 35 U.S.C. 154(b) by 534 days.

(21) Appl. No.: 14/516,988

(22) Filed: Oct. 17, 2014

(65) Prior Publication Data

US 2015/0037748 A1 Feb. 5, 2015

Related U.S. Application Data (63) Continuation-in-part of application No. 12/771,873, filed on Apr. 30, 2010.

(30) Foreign Application Priority Data

May 29, 2009 (EP) ..................................... 09161608

(51) Int. Cl.
*A61C 19/10* (2006.01)

(52) U.S. Cl.
CPC ........ *A61C 19/10* (2013.01); *A61C 2201/002* (2013.01)

(58) Field of Classification Search
CPC ....... A61C 19/004; A61C 19/10; A61C 1/088; A61N 2005/0652; A61B 1/06; A61B 1/24
USPC ..................................................... 433/26–29
See application file for complete search history.

(56) References Cited

U.S. PATENT DOCUMENTS

| | | | | |
|---|---|---|---|---|
| 3,405,446 A | * | 10/1968 | Wiener | ............... B29C 65/4825 433/215 |
| 3,436,157 A | * | 4/1969 | Adler | ................... A61B 5/0088 356/423 |
| 4,207,678 A | * | 6/1980 | Jeannette | ............... A61C 19/10 433/203.1 |
| 4,541,801 A | | 9/1985 | Mackert et al. | |
| 4,608,015 A | | 8/1986 | Smigel | |
| 4,620,841 A | * | 11/1986 | Farrell | ................... A61C 19/10 433/26 |

(Continued)

FOREIGN PATENT DOCUMENTS

| | | | | |
|---|---|---|---|---|
| CA | 22020559 | * | 10/1998 | ............. A61C 19/10 |
| CA | 2390407 A1 | * | 5/2001 | ............. A61C 19/10 |

(Continued)

OTHER PUBLICATIONS

J Prosthetic Dent. May 2003;89(5);453-61. Magne P1, Callucci Go, Celser UC., Anatomic crown width/length ratios of unworn and worn maxillary teeth in white subjects.*

(Continued)

*Primary Examiner* — Cris L Rodriguez
*Assistant Examiner* — Matthew Saunders
(74) *Attorney, Agent, or Firm* — Ann M. Knab; Thad McMurray (57) ABSTRACT

A dental color key having at least two different color patterns or samples with different tooth colors. The entire surface area of the color key (10) may be smaller than the buccal and/or labial surface area, that is to say the vestibular surface area of two teeth, and the color patterns or samples (12) are attached adjacent to one another and particularly mounted to one single tooth.

34 Claims, 6 Drawing Sheets

(56) References Cited

U.S. PATENT DOCUMENTS

| | | | |
|---|---|---|---|
| 4,887,906 A | 12/1989 | Koehler | |
| 4,919,617 A | 4/1990 | Antons et al. | |
| 5,177,694 A * | 1/1993 | Graham | A61C 19/10 356/421 |
| D344,588 S | 2/1994 | Park | |
| 5,482,464 A | 1/1996 | Shimosawa et al. | |
| 5,498,157 A | 3/1996 | Hall | |
| 5,639,235 A * | 6/1997 | Lapointe | A61C 13/082 433/215 |
| 5,685,712 A * | 11/1997 | Fischer | A61C 19/10 433/26 |
| 5,916,653 A | 6/1999 | Kunstadter et al. | |
| 6,007,332 A * | 12/1999 | O'Brien | A61C 19/10 356/404 |
| 6,139,318 A | 10/2000 | Foser | |
| 6,206,691 B1 * | 3/2001 | Lehmann | A61C 19/00 356/408 |
| 6,210,159 B1 * | 4/2001 | Lehmann | A61C 19/00 356/408 |
| 6,315,554 B1 | 11/2001 | Coste et al. | |
| 6,328,563 B1 | 12/2001 | Hobo | |
| 6,354,835 B1 * | 3/2002 | Maini | A61C 19/10 206/63.5 |
| 6,499,998 B2 | 12/2002 | Kerschbaumer et al. | |
| 6,575,751 B1 | 6/2003 | Lehmann et al. | |
| 6,743,014 B2 * | 6/2004 | Kerschbaumer | A61C 19/10 433/203.1 |
| 6,755,646 B2 | 6/2004 | Zun | |
| 6,802,714 B2 | 10/2004 | Cruz | |
| 6,848,904 B1 | 2/2005 | Vanini et al. | |
| 6,857,875 B1 * | 2/2005 | McClure | G09B 11/10 434/81 |
| 7,006,126 B2 * | 2/2006 | Kerschbaumer | A61B 1/24 348/61 |
| 7,522,322 B2 | 4/2009 | Blanding et al. | |
| 7,621,746 B2 | 11/2009 | Baughman | |
| 9,008,417 B2 * | 4/2015 | Rohner | G01J 3/02 382/165 |
| 2003/0124481 A1 | 7/2003 | Zun | |
| 2003/0148243 A1 * | 8/2003 | Kerschbaumer | A61B 1/00041 433/29 |
| 2003/0235799 A1 * | 12/2003 | Cruz | A61C 19/10 433/26 |
| 2004/0224278 A1 | 11/2004 | Zun | |
| 2004/0248057 A1 | 12/2004 | Culp | |
| 2005/0202362 A1 * | 9/2005 | Ostler | A61C 5/064 433/26 |
| 2005/0260535 A1 | 11/2005 | Costaras et al. | |
| 2005/0260536 A1 * | 11/2005 | Costaras | A61C 19/10 433/26 |
| 2006/0040230 A1 * | 2/2006 | Blanding | G01J 3/02 433/26 |
| 2007/0009855 A1 | 1/2007 | Stonisch | |
| 2007/0026363 A1 * | 2/2007 | Lehmann | A61C 13/0004 433/223 |
| 2008/0153054 A1 * | 6/2008 | Masters | A61C 19/10 433/26 |
| 2009/0246727 A1 | 10/2009 | Vanini et al. | |
| 2010/0238279 A1 * | 9/2010 | Thoms | A61B 1/00089 348/77 |
| 2011/0067190 A1 * | 3/2011 | Brattesani | A46B 15/0002 15/106 |
| 2014/0255867 A1 * | 9/2014 | Kim | A61C 19/10 433/26 |
| 2014/0272762 A1 * | 9/2014 | Weisz | A61C 19/10 433/26 |

FOREIGN PATENT DOCUMENTS

| | | | |
|---|---|---|---|
| DE | 2641740 A1 * | 3/1978 | A61C 19/10 |
| FR | 2823661 A1 * | 10/2002 | G01J 3/50 |
| JP | 2093060 A | 4/1990 | |
| JP | 6209959 A | 8/1994 | |
| JP | 2001008951 A | 1/2001 | |
| JP | 2001272276 A | 10/2001 | |
| JP | 2002262938 A | 9/2002 | |
| WO | 2007/034300 A1 | 3/2007 | |
| WO | WO 2012038474 A1 * | 3/2012 | A61C 5/14 |

OTHER PUBLICATIONS

Chu, S.J., Range and Mean Distribution Frequency of Individual Tooth Width of the Maxillary Anterior Dentition, Practical Procedures in Aesthetic Dentistry, May 2007, vol. 19, No. 4, pp. 209-215.

Wikipedia, "Sealant", Encyclopedia, pp. 1-3, https://en.wikipedia.org/wiki/Sealant, retrieved Apr. 5, 2017.

* cited by examiner

DENTAL COLOR KEY

CROSS-REFERENCE TO RELATED APPLICATIONS

This application is a continuation-in-part of U.S. Ser. No. 12/771,873, filed Apr. 30, 2010, which claims foreign priority benefits under 35 U.S.C. § 119(a)-(d) from European Patent Application EP 09 161 608.6 filed May 29, 2009, all of which are hereby incorporated by reference.

TECHNICAL FIELD

The invention relates to a dental color key having at least two color patterns or samples with different tooth colors.

BACKGROUND OF THE INVENTION

Dental color keys have been known for a long time. The color key according to U.S. Pat. No. 4,541,801 serves as an example. With a color key of this type, at least two different color patterns or samples with varying tooth colors are used and placed next to a neighboring tooth of the tooth to be restored. Each color sample typically has about the surface area of a tooth and often also has a curvature of its surface similar to a tooth.

Some more recent examples for dental color keys of this kind are solutions or approaches known from U.S. Pat. No. 5,653,589 and EP 1 002 502 A2. These solutions or approaches in fact represent improvements as the manageability of individual color patterns or samples and for this reason the possibility for the dentist to judge a color sample in relation to a natural tooth is improved. However, the result of comparison strongly depends on the subjective sensation or personal opinion of the dentist, and further for example also on the conditions of light exposure especially if a color sample of the color key is placed next to a tooth.

In particular the curvature of the color patterns or samples, which curvature is regarded as desired, requires a distinct three-dimensional design or configuration of the color patterns or samples such that a small color rod clearly projects even if it is placed or held next to a tooth. This already requires different light conditions as color sample and tooth then never are arranged on the same optical plane.

In order to exclude human influences on the judgement, it has been proposed to acquire an existing tooth color by use of a dental camera and to electronically select the suitable tooth color such as A2, A3 etc. For such a solution however it is necessary to perform complex calibration steps. An electronic color detection device of this kind is rather costly and therefore comes into consideration only with major dental practices.

The color keys known, purely for spatial reasons, typically merely comprise the most popular or established tooth colors that for example comprise no bleaching colors and even more no gingival colors.

OBJECTS AND SUMMARY OF THE INVENTION

On the other hand, the invention is based on the object to produce a dental color key having at least two color patterns or samples with different tooth colors, which color key is optimized with regard to color comparability, but nevertheless can be manufactured well-priced and nevertheless offers the possibility to cover a comparatively large spectrum.

This object is inventively solved by the dental color key comprising at least two color patterns or samples with different tooth colors, characterized in that the entire surface area of the color key is smaller than the buccal and/or labial surface, that is to say the vestibular surface of two teeth, and that the color patterns or samples are adjacent to one another The color key according to the invention is characterized by the fact that it comprises several, in particular a plurality of color patterns or samples, and in particular that it can be arranged in the peripheral region of a single adjacent tooth that is to be determined in terms of color. In this way, the regions of the tooth next to the color key can already be used for comparison purposes.

Due to the close proximity of a plurality of color patterns or samples with the tooth, the comparability can be clearly improved, because due to the immediate comparison, the comparability is considerably improved compared to the case that different small color rods are placed next to a tooth one after another out of one's memory.

Due to the fact that the color patterns or samples are notably small, said patterns or samples may also be attached close to the surface of the tooth that is to be defined. The extent of projection is not noteworthy, so that it may be assumed that the color patterns or samples are substantially arranged in the same plane just as the surface of the respective tooth.

According to the invention, however, it is preferred to attach or affix the miniaturized color key to a neighboring tooth, said attachment preferably being selected such that both central regions and marginal regions of the tooth to be determined are visible besides the miniaturized color key.

For example, there is the possibility to arrange the color key between teeth of the lower and upper jaw and to use it for the color comparison with the neighboring tooth. It is also possible to provide the inventive color key with a clip by means of which the color key may be attached at various positions of the dental lamella. The color key according to the invention is preferably small and lightweight and has a thickness of less than 6 mm, preferably 0.5 mm. The color patterns or samples preferably are within a grid or raster, particularly preferably within a matrix such that an easier allocation is possible.

This is also true if color options such as bleaching colors or gingival colors are provided at opposing lateral edges.

The standard color key preferably comprises four, in particular 16 color patterns or samples, next to which ridges with bleaching colors and gingival colors are attached if required.

An advantageous embodiment of the inventive color key provides that the color key occupies a surface area that is smaller than the vestibular surface area of a tooth. This particularly applies for incisors, that is to say for the labial surface area of incisors.

Even if it is preferred that 16 different color patterns or samples are realized in one color key, it is to be understood that in a modified embodiment any other number of color patterns or samples can be realized as well. This in particular applies if the color patterns or samples are not arranged in a discrete manner but continuously merge. Basically, it is also possible to leave a recess in the central part of the color key through which the vestibular surface is visible in order to keep the marginal distance small.

The color patterns or samples of the color key are preferably attached next to or on top of one another in a densely packed manner at a single tooth. This also provides for an especially favorable comparability due to the close distances. Alternatively, parting lines, in particular separating strips, may be provided that permit an optical separation of the individual color patterns or samples that either merge or run together continuously or that adjoin one another in a discrete manner.

The color patterns or samples of the color key may be realized in any suitable manner and may be supported for example by an opaque and/or dentin material.

A particular favorable refinement provides that the dental color key occupies a surface area that is smaller than a buccal and/or labial surface of a tooth, particularly smaller than a buccal or labial surface of a human tooth.

A particular favorable refinement provides that the color key comprises at least four, in particular sixteen different known dental color patterns or samples.

A particular favorable refinement provides that the color patterns or samples of the color key are built from a restoration material that has been dyed according to the tooth color.

A particular favorable refinement provides that the color patterns or samples of the color key comprise different color shades and opacities.

A particular favorable refinement provides that the color patterns or samples of the color key correspond to similar tooth colors of a color shade.

A particular favorable refinement provides that the color key comprises at least one color sample that corresponds to a bleach color and/or to a color of the gums or gingiva.

A particular favorable refinement provides that the color key may be arranged or is releasably mounted in the peripheral region of a tooth that is to be analyzed.

A particular favorable refinement provides that the color key forms part of a spacer that in particular interacts with a camera.

A particular favorable refinement provides that the color key and the buccal and/or labial surface area of the tooth that is to be analyzed, substantially extend into the same plane.

A particular favorable refinement provides that the color key is releasably mounted—in particular mechanically or adhesively—on at least one tooth or between at least two teeth of the upper jaw and the lower jaw.

A particular favorable refinement provides that the color key has a thickness of 0.01 mm to 6 mm and in particular is formed as a printed foil or film.

A particular favorable refinement provides that the foil or film is provided with an adhesive that can be removed from a tooth surface without leaving behind any remainders, i.e. in a residue-free manner.

A particular favorable refinement provides that at least the color patterns or samples at least partially are made from ceramics.

A particular favorable refinement provides that at least the color patterns or samples at least partially are made from a dental composite material.

A particular favorable refinement provides that the color patterns or samples continuously merge or run together.

A particular favorable refinement provides that the color patterns or samples do not continuously merge or run together but are represented in a discrete manner.

A particular favorable refinement provides the color patterns or samples regarded together are completely surrounded by an edge of the sealing material being used to seal the gaps between the color patterns or samples and the width of the edge being substantially equal to the width of the gaps between the color patterns or samples. It is preferable that the color patterns or samples extend above the sealing material and gaps so that the color patterns or samples are not flush with the gaps and sealing material.

A particular favorable refinement provides a sealing material disposed or applied on the gap.

A particular favorable refinement provides the color patterns or samples regarded together are completely surrounded by an edge of the sealing material being used to seal the gaps between the color patterns or samples and the width of the edge being substantially equal to the width of the gaps between the color patterns or samples.

A particular favorable refinement provides a dental color key wherein the color patterns or samples and the sealing edge regarded together are completely surrounded by an edge of the base body.

A particular favorable refinement provides a dental color key wherein the color variation between two adjacent color patterns or samples is little compared to the color variation between the lightest and the darkest color pattern or sample on the dental color key.

A particular favorable refinement provides a dental color key wherein the base body and/or the sealing material is fabricated of a color that comprises a common tooth color, wherein the common tooth color may include a tooth color that is exhibited by teeth in a majority of humans.

A particular favorable refinement provides a dental color key wherein a common tooth color may be a tooth color that is exhibited by teeth in a majority of the population on which dental work is being performed.

A particular favorable refinement provides a dental color key wherein a common tooth color is dependent upon the popular or common shades that are used by a dentist or lab technician to fabricate dental materials and restorations.

A particular favorable refinement provides a dental color key wherein the sealing between the adjacent color patterns or samples and the sealing surrounding the color patterns or samples is transparent.

A particular favorable refinement provides a dental color key wherein the upper surface of each of the individual color patterns or samples (12) are not covered with a coating or sealing material.

A particular favorable refinement provides a dental color key wherein the base body is made of a ceramic material.

A particular favorable refinement provides a dental color key wherein the color patterns or samples are arranged in a matrix-like manner with at least two rows and at least two lines such that the color patterns or samples form a spiral.

A particular favorable refinement provides a dental color key wherein the spiral starts in one center point with the lightest color pattern or sample of the dental color key and ending at one edge point of the base body with the darkest color pattern or sample of the dental color key.

A particular favorable refinement provides a dental color key wherein the spiral starts in one center point with the darkest color pattern or sample of the dental color key and ending at one edge point of the base body with the lightest color pattern or sample of the dental color key.

A particular favorable refinement provides a dental color key has a holder that is substantially dark in color.

A particular favorable refinement provides a dental color key wherein the holder is formed by a strap of metal or sheet metal.

A particular favorable refinement provides a dental color key wherein the base body is secured to the holder in a self-supporting manner.

A particular favorable refinement provides a dental color key wherein the base body protrudes from the front plane of the holder.

A particular favorable refinement provides a dental color key wherein the rear side of the base body is connected to the front plane of the holder, and the base body is arranged at the end of the holder being opposite to the end serving as a hand grip of the dental color key.

A particular favorable refinement provides a dental color key wherein the base body is rotatably mounted to the holder.

A particular favorable refinement provides a dental color key having at least twenty different known dental color patterns or samples.

A particular favorable refinement provides a dental color key wherein the edge of the base body is not covered and remains freely visible.

BRIEF DESCRIPTION OF THE FIGURES

Further advantages, details and features emerge from the following description of several exemplary embodiments of a dental color key according to the invention on the basis of the drawings, in which.

DETAILED DESCRIPTION

Figure 1:
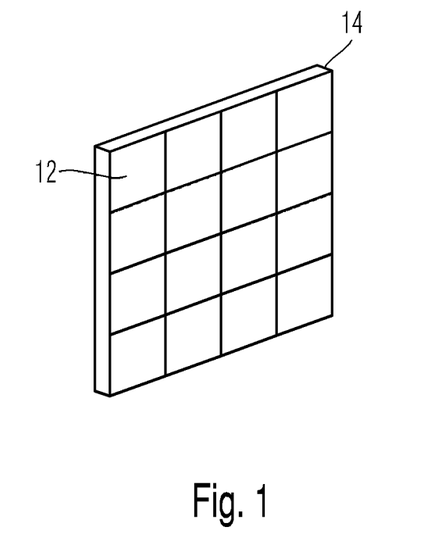
FIG. 1 shows a perspective view of an embodiment of an inventive color key in schematic representation.

The inventive dental color key 10 represented in FIG. 1 comprises a plurality of, for example, 16 color patterns 12 that are arranged in the manner of a matrix. Each color pattern corresponds to a commercial or standard tooth color such as A2, A3, A4 etc., and tooth colors similar to one another are preferably arranged adjacent to one another.

The color patterns 12 are fixedly mounted on the small plate shaped color key. In this respect, the color key comprises a thin base body 14 that is suitable for being mounted on a tooth, namely on the vestibular surface area thereof. The mounting can be effected either with the aid of an adhesive that retains the base body 14 in a manner such that it at least does not come loose in case of a soft nudge with the tongue, or with a clip that overlaps the tooth, preferably an incisor, and as a result provides for the desired clamping effect.

It is also possible to design the base body flexible to some extent such that it may better adapt itself to the slightly curved surface of the incisor. Preferably, the base body is notably smaller than a tooth, for example half the width thereof, and significantly thinner, for example more than one decimal power. As a result, the inventive color key 10 rests on the tooth with its entire face, and it is possible to enable an immediate comparison between the color pattern 12 and the tooth. In this respect, sufficient free areas of the vestibular surface of the tooth remain, whereas it is to be understood that a neighboring tooth may also be easily compared to the inventive color key 10.

The color patterns 12 of the color key 10 may be built from a restoration material that has been dyed according to the tooth color. The color patterns 12 of the color key 10 may also comprise different color shades and opacities. It is also possible to arrange the color patterns 12 of the color key 10 in such a manner that they continuously merge or run together.

Figure 2:
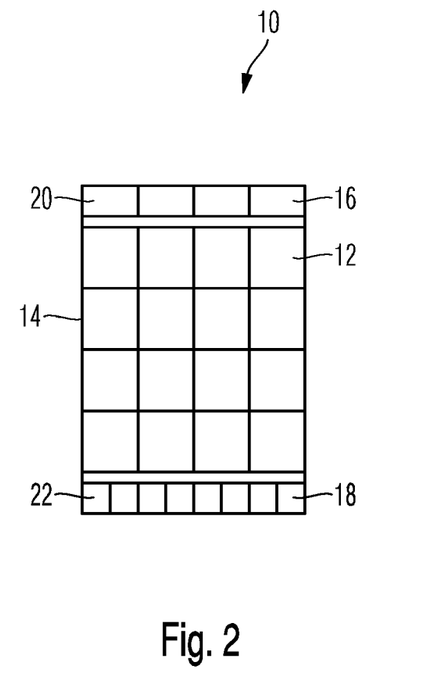
FIG. 2 shows a further embodiment of an inventive dental color key in a top view.

While FIG. 1 shows a color key having 16 color patterns, the color key of a further embodiment of the present invention, as shown in FIG. 2, includes 28 color patterns. Additionally to the 16 stock color patterns 12 this color key includes four color patterns 16 corresponding to four bleach colors, respectively, as well as eight color patterns 18 corresponding to eight gingival colors, respectively. These color patterns 16 and 18 are arranged in the embodiment shown in FIG. 2 by means of separate base bodies 20 and 22, wherein both of the base bodies 20 and 22 are kept pluggable on the base body 14. It is also possible and conceivable to realize the color key including four color patterns 16 as an entity, which achievement may be also more inexpensive as the embodiment shown in FIG. 2.

By the elected longitudinal arrangement of the dental color key according to FIG. 2, it is ensured that the edge distance of also the internal color patterns 12 is not too large and in addition, that the color key 10 does not tower above the vestibular surface of the tooth. For this purpose, it is preferred that the color key 10 is vertically attached, as shown in FIG. 2. Further, it is preferred that the base body 22 is assembled in such a way that the color patterns 18 corresponding to gingival colors are arranged apically.

Figure 3:
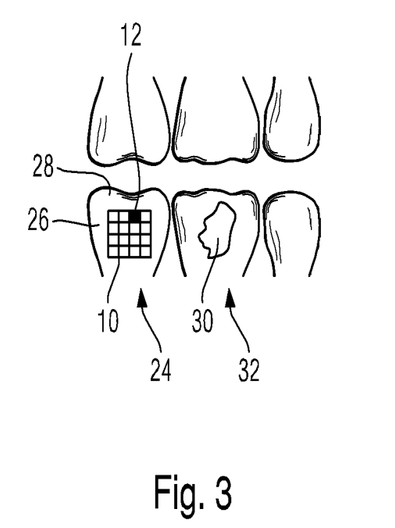
FIG. 3 shows a top view of an inventive dental color key after having been attached to a tooth.

FIG. 3 shows in which manner an inventive color key 10 may be mounted on a tooth 24. In the represented embodiment, the color key 10 is centrally mounted on the vestibular face 26 of the tooth such that free faces 28 surround the color key 10 at all sides thereof.

By means of an optical comparison—either direct or with auxiliary equipment—one manages to detect the match of a color pattern 12 with a surface 30 of a neighboring tooth 32 such that the tooth color for this surface area 30 is determined and thus detected.

It is particularly favorable if in case of a photographic support, this is realized with the same photograph, as no calibration is then required but the respective tooth color is detected automatically.

Figure 4:
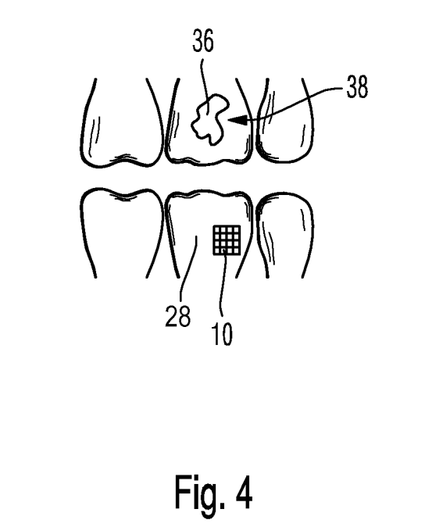
FIG. 4 shows a top view of a further embodiment of an inventive dental color key after having been attached to a tooth.

In FIG. 4 it is represented in which a color key 10 is used in order to detect an area 36 of an antagonist tooth 38. In the embodiment represented, the color key 10 is distally mounted on the vestibular face or surface of the tooth such that there are comparatively large free or open areas 28 at three sides that are particularly well suitable for assessing the tooth color.

Figure 5:
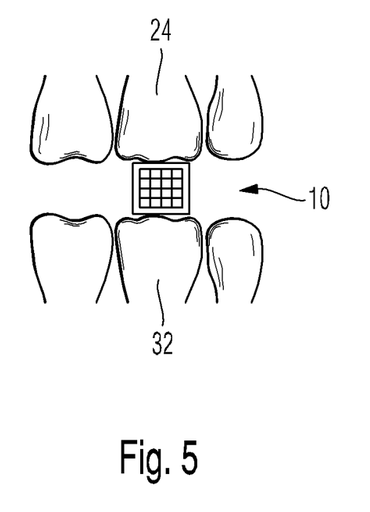
FIG. 5 shows a modified arrangement of an inventive dental color key.

FIG. 5 shows a modified embodiment of an inventive dental color key 10, which embodiment allows to assess as well as possible both a lower jaw tooth and its upper jaw antagonist. For this reason, a dental color key according to FIG. 9 is clipped on both the lower jaw and the upper jaw and thus allows judging or assessing both the tooth 24 and the tooth 32 in a similar manner.

Figure 6:
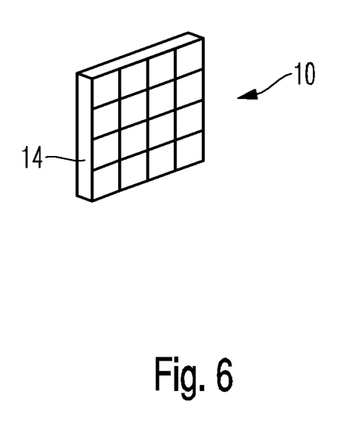
FIG. 6 shows a dental color key in a further embodiment, said dental color key being configured as a small plate or disk.
Figure 8:
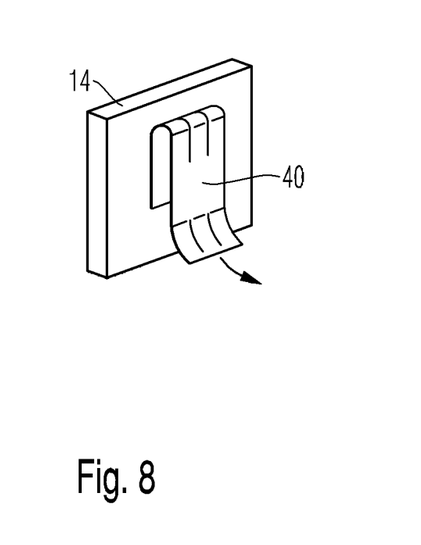
FIG. 8 shows a dental color key according to FIG. 6 shown from the rear side and having a fastening clip.

FIG. 6 shows that the inventive dental color key 10 with its base body 14 may have the shape of a thin plate that according to FIG. 8 may be well clipped on a tooth and located in position there with the aid of a clip 40 that is mounted on the rear side of the thin plate.

Figure 7:
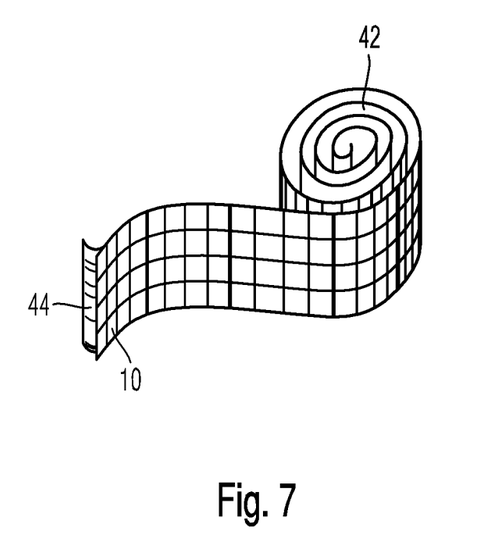
FIG. 7 shows a multiple arrangement of dental color keys that are formed like a film and that are wound up on a roll.

A modified embodiment of an inventive dental color key is represented in FIG. 7. In this case, the dental color key 10 is mounted on a roll 42 like an adhesive label, and a common carrier film 44 is designed in such a manner that the dental color key 10 that is coated with an adhesive surface on its back side, may easily be separated from the carrier film 44.

Figure 9:
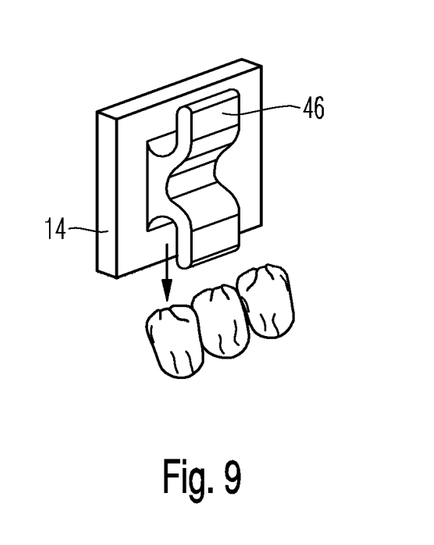
FIG. 9 shows a different fastening device for a dental color key.

FIG. 9 shows a double clip that allows for the specific arrangement of the dental color key according to FIG. 5, said double clip 46 being capable of engaging over both a lower jaw incisor and an upper jaw incisor as can be seen from the drawing, and keeping both teeth in a defined distance from one another.

Figure 10:
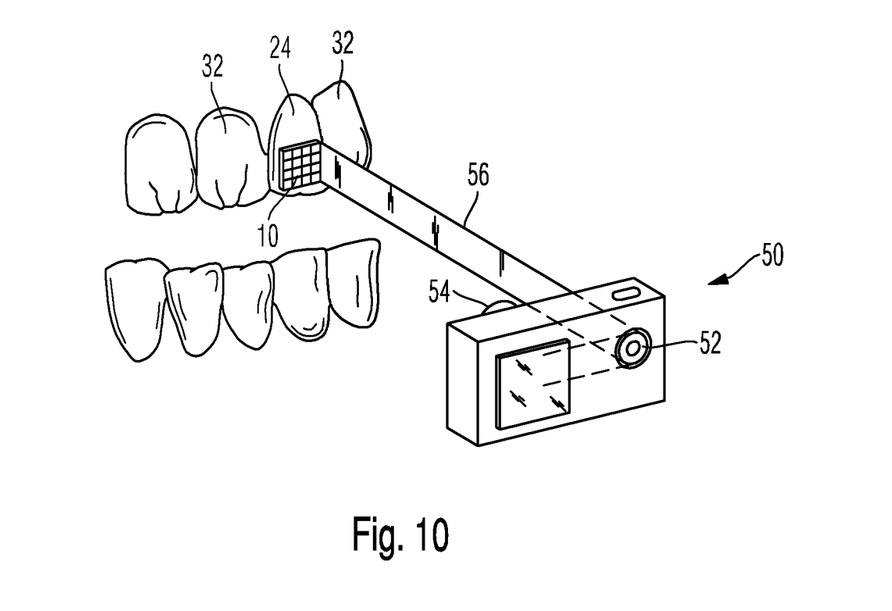
FIG. 10 shows a tooth color analyzing device for use with an inventive dental color key.
Figure 11:
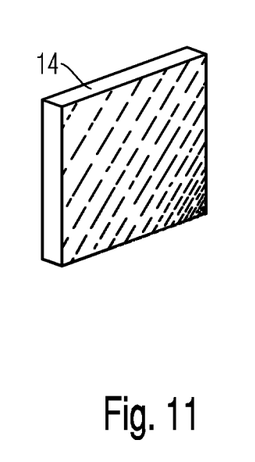
FIG. 11 shows color patterns/samples that continuously merge together.

FIG. 10 represents a dental analyzing device 50 that takes and stores a picture of the dental color key 10 together with the tooth 24 and typically also of the neighboring teeth 32 via a lens 54 having a CCD sensor. A spacer 56 is shown between the camera 50 attached by fixing means 52 to camera 50 and tooth 24.

As a result, a calibration of the dental analyzing device 50 can be avoided in a particularly favorable manner.

According to a further embodiment of the present invention which is not shown in the FIGS. 1 to 11, it is also possible to arrange the color key on a spacer that in particular interacts with a dental camera.

In one preferred embodiment, which is illustrated in the drawings FIGS. 12 to 16 the dental color key (10) comprises a holder 60, a base body 14 carrying twenty individual samples of dental colors 12 arranged in a matrix of four lines and five rows. The samples 12 are fixedly mounted on the base body 14 in a suitable manner, e.g. glued to it. In this manner, the base body 14 acts as a carrier plate for the samples of dental colors 12. The samples 12 are arranged such that gaps remain between adjacent samples. The gaps between the individual samples of dental colors 12 are all substantially the same width. The actual size of the color key may be smaller than, similar to, or larger than the size of a human tooth. One preferred embodiment is that the color key be slightly larger than a human tooth, preferably slightly larger than the size of an average adult human tooth or about the size of two average human teeth. It is preferable that the color key be of a size such that it can be easily situated near a person's tooth such that all of the colors on the grid can be seen and easily compared to a spot on a person's tooth, but not too large such that it would not fit in a patient's mouth. The combination of the optimal size of the color grid, the layout of the colors in grid form, the display of two or more colors, preferably 16 to 20 colors in a compact grid format displaying a number of color shades to match a person's tooth provides a facile and efficient color system for determining a patient's tooth color.

Figure 12:
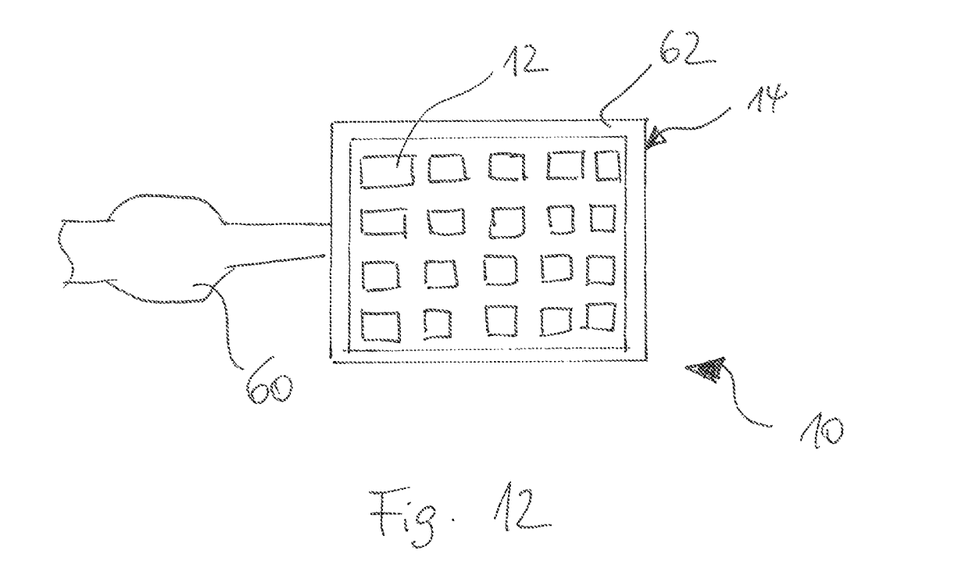
FIG. 12 shows a further embodiment of an inventive dental color key in a top view.

The samples of dental colors 12 are preferably made of small square-cut ceramic plates fabricated of the same dental restoration material which is used for producing the dental restoration parts later on. In this way, the tooth colors being represented by these samples of dental colors 12 very closely match the color of the dental restoration which is finally to be inserted into a patient's mouth. Therefore, it is of great importance that these samples of dental colors 12 arranged on the base body 14 are not covered at all by any coating (e.g. varnish, finish, lacquer, etc.). It is understood that also a coating that will not influence the perception of the color of the respective color samples (12) can be used to protect the color samples.

The base body 14 can be made of any suitable material, e.g. ceramic. It is preferable that the base body is made of a material that is used to make dental restorations. It has been found that the color as well as the opacity of the base body is of great importance for providing a good shade/color match to the patient's teeth with respect to both manual detection and computer-aided detection. Thus, it is possible to make the base body 14 with a material that is the color/shade of a common tooth color according to one of the widely used dental color keys, e.g. tooth color A3. The color/shade of the base body and/or sealing material is not limited to this color, but may be any color or shade used in the dental industry to match a person's tooth color. It is preferred that the colors are based on human tooth colors. Commonly used shade guides include the Vita shade guide having for example, shades such as B1, A1, B2, D2, A2, C1, C2, D4, A3, D3, B3, A3.5, B4, C3, A4, C4, and also bleach shades such as 0M1, 0M2, 0M3, BL1, BL2, BL3, BL4. Various shade guides used in the industry include, but are not limited to, VITA Classical Shade Guide, Bleachedguide 3D-Master, VITA Linearguide 3D-Master, VITA 3D-Master Shade Guide, and VITABLOCS Guide 3D-Master, all by Vident, Inc. Brea, Calif. However, any other color can be suitable as long as the detection of the tooth color of the natural tooth to be analyzed can be achieved easily both manually or with the aid of a device, e.g. a camera and/or a computer. It is to be understood that the color of the base body can be of any kind such that it does not influence the color detection in an undesirable manner.

By mounting the individual samples of dental colors 12 on the base body 14 the correct positioning of the samples of dental colors 12 can be ensured. Each one of the samples of dental colors 12 is placed such that a gap remains between each of the samples of dental colors 12. This gap is vital for avoiding any influence or interference of adjacent samples of dental colors 12. Preferably, this gap is sealed with a sealing material 64, in order to e.g. avoid contamination, uncleanliness, etc., in the gap areas. Additionally, the entirety of the matrix of the twenty samples of dental colors 12 (being arranged for example in a 4×5 matrix) is further completely surrounded by an edge 66, which is preferably made of the same sealing material which is used for filling the gaps between the samples of dental colors 12, as described above. The width of the edge 66 is substantially the same as the width of the gaps between the samples of dental colors 12. It is to be understood that any other suitable material for the edge (66) can be used to surround the matrix of dental colors.

It has been found that also the color and opacity of the sealing material being used as the sealing material 64 between the samples of dental colors 12 as well as for the edge 66 surrounding the matrix of the samples of dental colors 12 is of great importance for good color detection results. All the aforementioned characteristics and requirements of the color of the base body 14 apply also to the color of the sealing material. However, in one especially preferred embodiment the sealing material is transparent which means that the color of the base body 14 can be seen through the sealing material.

Surrounding the edge 66 of the sealing material in turn is another edge 62 of the material of the base body 14 which has been left uncovered both by samples of dental colors 12 and sealing material. Thus, further to the carrying function of the base body 14, the latter is also important for mechanically protecting the samples of dental colors 12 as well as for suppressing scattering light (from the side, from behind) which would otherwise worsen the color detection results.

Furthermore, the holder 60, which is preferably made of metal or sheet metal can be connected to the base body either firmly (e.g. being glued to it) or in a rotatable manner by any suitable connection or joint. Preferably, the rotational axis runs perpendicularly to the mounting surface of the base body (carrying the samples of dental colors 12). By means of this rotatable connection, it becomes possible to pivot any sample of dental colors 12, which is mounted adjacent to the edge of the base body 14 to the natural tooth being analyzed, as well as to its neighboring tooth, in order to ease the color detection (by bringing it closer to the tooth color to be detected).

Figure 13:
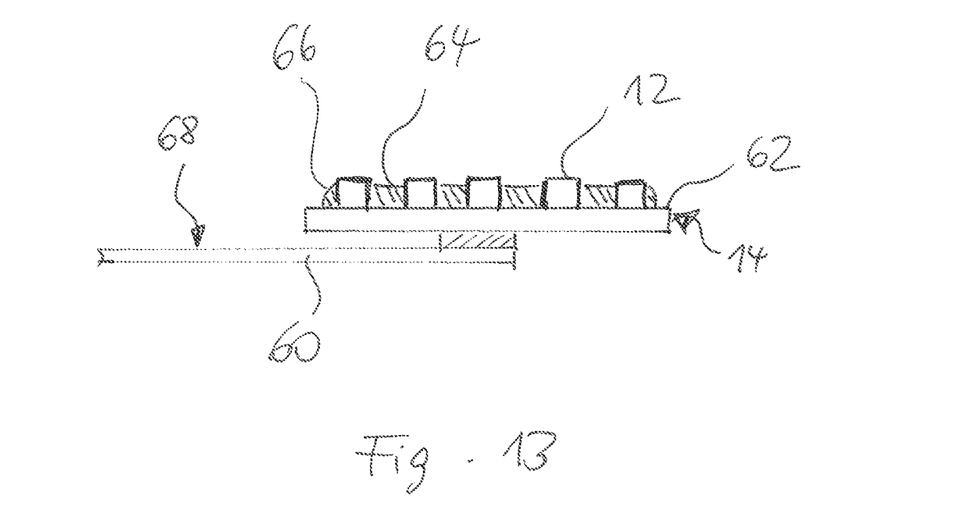
FIG. 13 shows a side view of a dental color key according to FIG. 12.

Reference is made to the embodiment illustrated in FIG. 13, wherein the dental color key 10 protrudes from the plane being defined by the front surface 68 of the holder 60. This makes it possible to place the dental color key 10 very close to the natural tooth to be analyzed such that the holder 60 is placed next to the buccal surface of the natural tooth to be analyzed (or even in the gap between two natural teeth) and the base body 14 with its back placed very closely to the buccal surface of the natural tooth. In essence, the front surface of the base body 14 carrying the samples of dental colors 12 can be placed almost in the same plane as the plane of the buccal surface of the natural tooth to be analyzed thus minimizing the distance between these two afore mentioned planes and further decreasing undesired impact of different illumination conditions (which could be caused by two different illumination planes). The samples of dental colors 12 can thus be brought very closely to the surface of the tooth to be analyzed.

Figure 14:
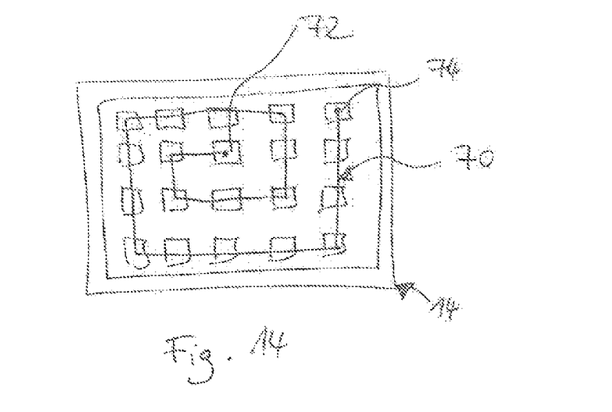
FIG. 14 shows a top view of an inventive color key showing the spiral formation of the color shades.
Figure 15:
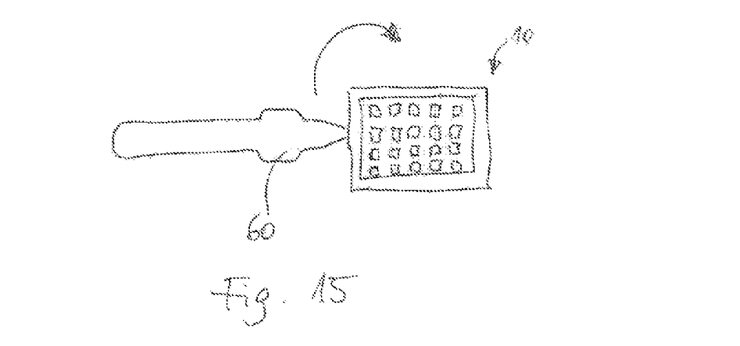
FIG. 15 shows the dental color having an alternate holder.
Figure 16:
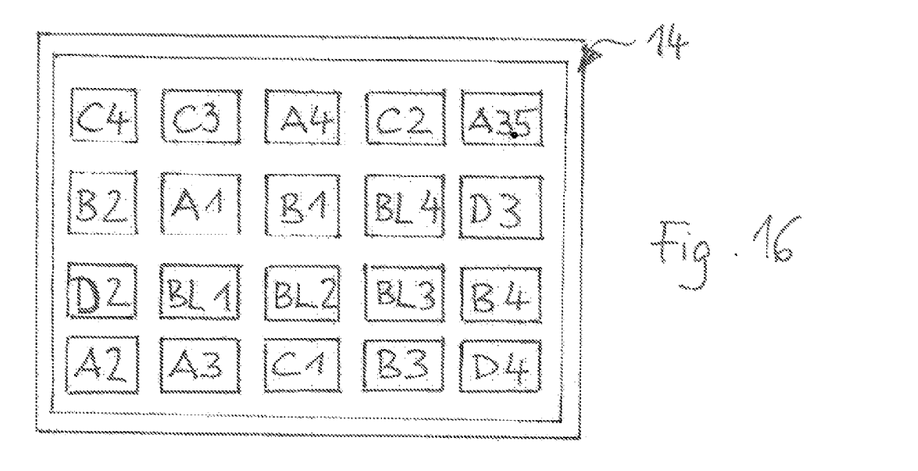
FIG. 16 shows an example of a spiral formation of color shades.

FIG. 14 illustrates a preferred arrangement of the individual samples of dental colors 12 such that it virtually forms a spiral 70 starting at one edge point 74 and running to a point 72 being situated near the center of the matrix of dental colors. It has been found that improved detection results can be achieved if tooth colors which are very close together with respect to lightness and similar colors are being placed adjacent to one another. These very similar colors of the dental color samples (12) are preferably arranged such that not only the dental color samples (12) with directly preceding and subsequent dental color samples (12)—with respect to the course of the spiral (70)—have a very small color distance or variation one to the other but also the adjacent dental colors (regarded in the lines and columns of the matrix). Thus, interferences between the colors of the individual dental color samples (12) can be reduced to a great extent. For a better understanding one possible arrangement of dental color samples is illustrated in FIG. 16. This illustration by no means limits the possibilities of arrangements of colors in the matrix. The spiral arrangement allows for easy comparison and aids the practitioner in assessing the closest color match to the patient's tooth to be restored.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A dental color key comprising a holder and at least two color patterns or samples with different tooth colors mounted on a common base body, characterized in that
    the color patterns or samples (12) are adjacent to one another and are spaced apart such that a gap exists between the at least two color patterns or samples (12) wherein the gap is sealed with a sealing material (64),
    the color patterns or samples (12) regarded together are completely surrounded by an edge (66) of the sealing material being used to seal the gaps between the color patterns or samples (12) and the width of the edge being substantially equal to the width of the gaps between the color patterns or samples (12),
    wherein the color key is larger than one adult human tooth and smaller than two adult human teeth, and
    wherein the color patterns or samples extend above the gap and the sealing material.

2. The dental color key as claimed in claim 1, wherein the color key (10) comprises at least four different known dental color patterns or samples (12).

3. The dental color key as claimed in claim 1, wherein the color patterns or samples (12) and the sealing edge (66) regarded together are completely surrounded by an edge (62) of the base body (14).

4. The dental color key according to claim 1, wherein the color variation between two adjacent color patterns or samples (12) is less when compared to the color variation between the lightest and the darkest color pattern or sample (12) on the dental color key (10).

5. The dental color key according to claim 1, wherein the base body is fabricated of a color that comprises a common tooth color found in dental shade guides.

6. The dental color key according to claim 5 wherein a common tooth color comprises a tooth color that is exhibited by teeth in humans.

7. The dental color key according to claim 5 wherein a common tooth color comprises a tooth color that is exhibited by teeth in a population on which dental work is being performed.

8. The dental color key according to claim 1, wherein the sealing between the adjacent color patterns or samples (12) and the sealing surrounding the color patterns or samples (12) is transparent.

9. The dental color key according to claim 1, wherein the sealing between the adjacent color patterns or samples (12) and the sealing surrounding the color patterns or samples (12) is fabricated of a color that comprises a common tooth color found in dental shade guides.

10. The dental color key according to claim 9 wherein a common tooth color comprises a tooth color that is exhibited by teeth in humans.

11. The dental color key according to claim 9 wherein a common tooth color comprises a tooth color that is exhibited by teeth in a population on which dental work is being performed.

12. The dental color key according to claim 1, wherein an upper surface of each of the individual color patterns or samples (12) are not covered with a coating or sealing material.

13. The dental color key according to claim 1, wherein the base body (14) is made of a ceramic material.

14. The dental color key according to claim 1, wherein at least four color patterns or samples (12) are arranged in a matrix-like or grid manner with at least two rows and at least two lines such that the color patterns or samples (12) form a spiral (70).

15. The dental color key according to claim 14, wherein the spiral (70) starts in one center point (72) with the lightest color pattern or sample (12) of the dental color key (10) and ending at one edge point (74) of the base body (14) with the darkest color pattern or sample (12) of the dental color key (10).

16. The dental color key according to claim 14, wherein the spiral (70) starts in one center point (72) with the darkest color pattern or sample (12) of the dental color key (10) and ending at one edge point (74) of the base body (14) with the lightest color pattern or sample (12) of the dental color key (10).

17. The dental color key as claimed in claim 1 wherein the holder (60) is colored in a dark color.

18. The dental color key as claimed in claim 17 wherein the holder (60) is formed by a strap of metal or sheet metal.

19. The dental color key as claimed in claim 18 wherein the base body (14) carrying the at least two color patterns or samples (12) is secured to the holder (60) in a self-supporting manner.

20. The dental color key as claimed in claim 14 wherein the base body (14) carrying the at least two color patterns or samples (12) protrudes from the front plane (68) of the holder (60).

21. The dental color key as claimed in claim 20 wherein
a rear side of the base body (14) is connected to a front plane (68) of the holder (60), and
the base body (14) is arranged at an end of the holder (60) being opposite to an end serving as a hand grip (80) of the dental color key (10).

22. The dental color key as claimed in claim 21 wherein the base body (14) is rotatably mounted to the holder (60).

23. The dental color key as claimed in claim 2, wherein the color key (10) comprises at least twenty different known dental color patterns or samples (12).

24. The dental color key as claimed in claim 1, wherein the color key (10) comprises at least sixteen different known dental color patterns or samples (12).

25. The dental color key as claimed in claim 3, wherein the edge (62) of the base body (14) is not covered and remains freely visible.

26. The dental color key as claimed in claim 1, wherein the color patterns or samples (12) of the color key (10) are built from a restoration material that has been dyed according to the tooth color.

27. The dental color key as claimed in claim 1, wherein the color patterns or samples (12) of the color key (10) comprise different color shades and opacities.

28. The dental color key as claimed in claim 1, wherein the color patterns or samples (12) of the color key (10) correspond to similar tooth colors of a color shade.

29. The dental color key as claimed in claim 1, wherein the color key (10) comprises at least one color sample corresponding to a bleach color (16), a color of the gums or gingiva, or both a bleach color and a gum or gingiva color.

30. The dental color key as claimed in claim 1, wherein the color key (10) may be arranged or is releasably mounted in the peripheral region of a tooth that is to be analyzed.

31. The dental color key as claimed in claim 1, wherein the color key (10) may extend into the same plane as a buccal and/or labial surface area (26) of a tooth that is to be analyzed.

32. The dental color key as claimed in claim 1, wherein at least the color patterns or samples (12) at least partially are made from ceramic material and/or a dental composite material.

33. The dental color key as claimed in claim 1, wherein the color patterns or samples (12) of the color key (10) are built from a restoration material that has been dyed according to the tooth color.

34. The dental color key as claimed in claim 1, wherein the color key (10) forms part of a spacer that in particular interacts with a camera.

* * * * *